US005663152A

United States Patent [19]
Hayano et al.

[11] Patent Number: 5,663,152
[45] Date of Patent: Sep. 2, 1997

[54] POTENTIATORS FOR AMINOGLYCOSIDES

[75] Inventors: Fusakazu Hayano, Riverside, Conn.; Isao Kubo, Moraga, Calif.

[73] Assignee: Asahi Kasei Kogyo Kabushiki Kaisha, Osaka, Japan

[21] Appl. No.: 375,433

[22] Filed: Jan. 19, 1995

[51] Int. Cl.$^6$ .................................................. A61K 31/70
[52] U.S. Cl. .................................. 514/38; 514/39; 514/40
[58] Field of Search ................................ 514/40, 39, 38, 514/37

[56] References Cited

U.S. PATENT DOCUMENTS

| 4,241,098 | 12/1980 | Mussinan et al. | 426/534 |
|---|---|---|---|
| 4,526,888 | 7/1985 | Williams et al. | 514/12 |
| 5,079,234 | 1/1992 | McGregor et al. | 424/78.31 |

*Primary Examiner*—Elli Peselev
*Attorney, Agent, or Firm*—Pennie & Edmonds LLP

[57] ABSTRACT

The present invention provides antimicrobial compositions, especially compositions comprising an antimicrobial (microbiocidal or microbiostatic) compound and a potentiator of antimicrobial activity. Compositions of the invention combinating an antimicrobial compound and a potentiator are able to kill or inhibit the growth of microorganisms using much lower concentrations of the antimicrobial compound. The potentiator also enhances the efficacy of antimicrobial compounds against resistant strains of the microorganism.

7 Claims, No Drawings

POTENTIATORS FOR AMINOGLYCOSIDES

1. FIELD OF THE INVENTION

The invention pertains to antimicrobial compositions, in particular to compositions comprising a microbiocidal or microbiostatic compound and a potentiator of antimicrobial activity.

2. BACKGROUND

The aminoglycosides are a group of bactericidal antibiotics derived from species of Streptomyces or Micromonosporum and characterized by two or more amino sugars joined by a glycoside linkage to a central hexose. Aminoglycosides act by causing misreading and inhibition of protein synthesis on bacterial ribosomes and are strongly effective against Gram-negative bacilli, Gram-positive bacilli, and tubercular bacilli. The administration of aminoglycoside antibiotics, however, sometimes poses serious side effects such as nephrotoxicity, ototoxicity, or neuromuscular blockade (Goodman and Gilman's The Pharmacological Basis of Therapeutics, Eighth Edition, Pergamon Press pp 1098–1116). Therefore, there is a strong need for compositions having all of the beneficial properties of aminoglycoside antibiotics, but with reduced side effects.

Higher plants are known to produce various antimicrobial agents, which may be identified as new drugs with novel chemical structures, and new mechanisms of action. These kinds of "natural" medicinal products are strongly desired by today's environmentally-aware consumers.

3. SUMMARY OF THE INVENTION

The present invention has been accomplished by evaluating the antimicrobial activity of combinations of plant-derived compounds and aminoglycoside antibiotics. Because the combinations of more than two compounds may prevent or supress the emergence of resistant strains, it is generally superior to the use of a single compound.

The present invention provides antimicrobial compositions comprising synergistic combinations of an antimicrobial (microbiocidal or microbiostatic) compound and a potentiator of antimicrobial activity derived from higher plants. Compositions of the invention combining an antimicrobial compound and a potentiator are both microbiocidal and microbiostatic. Thus, the compositions according to the invention are able to kill microorganisms or inhibit the growth of microorganisms using much lower concentrations of the antimicrobial compound, providing reduced side effects. The potentiator also enhances the efficacy of antimicrobial compounds against resistant microbial strains.

Exemplary antimicrobial compositions according to the invention comprise aminoglycoside antibiotics such as Gentamicin, Streptomycin, Kanamycin, Fradiomyctn, Paromomycin, Tobramyctn, Netilmicin, Amikacin, Neomycin, Ribostamycin, Dibekacin, Sisomicin, Micronomtcin, Isepamtcin, Bekanamycin, or Astromicin in combination with an anethole potentiator. Such antimicrobial compositions are effective against Gram-negative bacilli such as *Escherichia coli*.

Other exemplary antimicrobial compositions according to the invention comprise aminoglycoside antibiotics in combination with an indole or 2-hexenal potentiator. Such antimicrobial compositions are effective against both Gram-negative bacilli and Gram-positive bacilli such as *Escherichia coli, Pseudomonas aeruginosa*, and methicillin resistant *Staphylococcus aureus*.

The invention also provides methods for inhibiting the growth of microorganisms by contacting the microorganism with an antimicrobial composition according to the invention.

The potentiators by themselves usually exhibit weak antibiotic activity. However, the combination of a potentiator and an antibiotic component has synergistic antibiotic activities which enable use of reduced amounts of the antibiotic component.

Compositions comprising an antibiotic component and a potentiator may be used to treat in vivo infections, or to disinfect topical surfaces such as bandages, bodily appliances, catheters, surgical instruments and patient examination tables.

For treatment of in vivo infections, the compositions may be administered either internally or externally. For external administration, the compositions may be used to treat infections of skin or mucosal surfaces, infected cuts, burns, or abrasions, or bacterial skin infections. For internal administration, the compositions are useful for treating systemic bacterial infections, especially Staphylococcus infections. Other compositions may be administered internally by topical administration to mucosal surfaces.

Compositions for in vivo administration may be provided as solutions, especially aqueous solutions, but optionally may include alcoholic solutions to increase the solubility of hydrophobic components. Such solutions are convenient for oral administration but may be formulated for parenteral administration. For oral administration, ethanol is preferred because of its low toxicity. Usually ethanol will be present in the minimum concentration needed to keep the components in solution. For external topical application, isopropanol also may be used. Other formulations for oral administration may include solid dosage forms such as tablets or capsules including timed release formulas. Compositions preferred for topical administration may be provided as emulsions, suspensions, creams, or liposome dispersions, or as an ointment in a hydrophobic carrier such as petrolatum.

For topical disinfection of nonliving surfaces, compositions may be provided as solutions, either aqueous or organic. Where direct human contact with the disinfectant is to be limited, such as in disinfection of work surfaces or restrooms, mixed organic solutions may be appropriate, e.g., ethanol or isopropanol in water. Preferred alcohol solvents include ethyl, n-propyl, isopropyl, n-butyl, isobutyl, and t-butyl alcohols. Concentration of the alcohol in a mixed solvent system may range from 5% to essentially 100%. Usually the cosolvent will be water or an aqueous buffer. In most cases, the alcohol component will be limited to an amount necessary to keep the antibiotic and potentiator in solution.

The invention further comprises methods for the treatment of animals in need of treatment for a microbial infection by administration of the composition according to the invention, as heretofor described, either internally or externally. In a preferred embodiment, the animal to be treated is a human.

4. DETAILED DESCRIPTION OF THE INVENTION

The present invention provides pharmaceutical compositions comprising an antibiotic and a potentiator of antibiotic activity. Compositions of the invention are useful in suppressing the growth or infectivity of microorganisms which may be resistant to the antibiotic in the absence of potentiators. The antibiotic component of the compositions may be an aminoglycoside antibiotic. The potentiator of antibiotic activity may be an anethole, indole or a 3-alkyl indole, or an alkenyl aldehyde such as 2-hexenal.

The invention also provides methods of inhibiting the growth of microorganisms by contacting the microorganisms with compositions of the invention. These methods are effective against infections in vivo. This is demonstrated by test data showing the minimum inhibitory concentrations ("MIC") and minimum biocidal concentration ("MBC") of compositions against various pathogenic organisms cultured in vitro under standard conditions. These in vitro tests strongly correlate with in vivo activity, as is evidenced by the widespread use of the MIC and MBC determinations to predict utility of antimicrobial compositions in treatment of infection in animals, including humans. The methods also disinfect external surfaces, including intact skin, countertops, medical instruments, bandages and wound dressings, and the like.

A particular advantage of these compositions is their reduced toxicity. Because of synergy between the antibiotic and potentiator components, the amount of antibiotic required is reduced. Since the antibiotics are toxic both to humans and the environment, the reduced use of antibiotics is highly desirable.

In addition, the potentiators are relatively less toxic than conventional antibiotics; many of them, such as anethole, indole, and 2-hexenal, occur naturally in foods and are routinely consumed in the diet without apparent harm. Therefore pharmaceutical compositions comprising these potentiators are expected to have low toxicity as well.

Moreover, the combinations of different types of antimicrobial agents, such as aminoglycoside antibiotics and potentiators originating from higher plants, are superior to the use of a single antimicrobial compound, because the combination antimicrobial compositions can better prevent or supress the emergence of resistant strains.

The effective concentration of the potentiators is at least 200 µg/ml for anethole and indole and at least 100 µg/ml for 2-hexenal. In such concentration the potentiators can enhance the efficacy of antibiotics.

4.1. FORMULATIONS

Compositions of the invention may be provided as topical disinfectants for sterilization of surfaces such as countertops, surgical instruments, bandages, and skin; as pharmaceutical compositions, including by way of example, creams, lotions, ointments, or solutions for external application to skin and mucosal surfaces, including the Cornea, dermal cuts and abrasions, burns, and sites of bacterial or fungal infection; as pharmaceutical compositions, includingbyway of example creams, lotions, ointments, emulsions, liposome dispersions, tablets, or solutions, for administration to internal mucosal surfaces such as the oral cavity or vagina to inhibit the growth of bacteria; and as pharmaceutical compositions such as creams, gels, or ointments for coating indwelling catheters and similar implants which are susceptible to harboring bacterial infection.

For external application to intact skin or for disinfection of nonliving surfaces, an organic solvent or cosolvent such as ethanol or propanol may be employed. Evaporation of the solvent leaves a residue of the antibiotic and potentiator on the treated surface to inhibit reinfection.

Although the potentiator components frequently occur as components in food, for most uses a food or unpurified plant source does not adequately substitute for a partially or even highly purified potentiator in formulations of the invention. The additional components present in plant sources often contain undesirable components as well as the potentiator.

4.2. ANETHOLE

A preferred potentiator of antimicrobial activity is anethole.

The natural anethole may be obtained conveniently by isolation from the star aniseed oil.

Anethole is commonly used not only as an aromatic in food, confectionery, or drinks, but also as a stomachic.

Anethole is particularly effective in combination with an aminoglycoside antibiotic such as Gentamicin, Streptomycin, Kanamycin, Fradiomycin, Paromomyctn, Tobramycin, Netilmicin, Amikacin, Neomycin, Ribostamycin, Dibekacin, Sisomicin, Micronomicin, Isepamtcin, Bekanamycin, or Astromtcin, to generate compositions inhibiting *Escherichia coli*.

4.3. INDOLE AND 2-HEXENAL POTENTIATORS

Indole and 3-substituted indoles are effective potentiators in combination with an aminoglycoside antibiotic. Active indole derivatives include 3-alkyl indoles, especially the 3-methyl (skatole) or 3-ethyl derivatives, and also the 3-carboxylic derivative. 2-hexenal, which commonly exists in natural products, is also an effective enhancer.

5. EXPERIMENTAL PROCEDURES

5.1. TEST MICROORGANISMS

Microorganism strains were supplied by the ATCC. *Staphylococcus aureus* is a clinically significant member of the gram-positive group of bacterial pathogens. It gives rise to serious infections, and may produce bacteremia, endocarditis, and meningitis. Methicillin-resistant strains of *Staphylococcus aureus* were chosen for evaluation because they present a significant medical problem, in view of the fact that methicillin is the drug of choice for treatment of *S. aureus* infection in the common penicillin-resistant strains.

*Pseudomonas aeruginosa* was also chosen for evaluation. *P. aerugtnosa* is a gram-negative pathogenic bacillus which may cause urinary tract infections or pneumonia.

*Escherichia coli* is also a gram-negative pathogenic bacillus which may cause enteritis, peritonitis, or cystitis.

5.2. METHODS OF TESTING

5.2.1. MINIMUM INHIBITORY CONCENTRATION DETERMINATION

The MICs were determined by the broth dilution method (Kubo et al. J. Agric. Food Chem. 1992, 40, 245–248). Test compounds were dissolved in Di-Methyl Formamide ("DMF") to make stock solution at concentrations of 80, 40, 20, or 10 mg/ml depending upon the potency and solubility. An aliquot of 0.01 ml of the stock solution was added to a tube containing 0.99 ml of media to get the initial concentration of testing solution. Serial two-fold dilutions were made by mixing 0.5 ml of testing solution with 0.5 ml of blank medium. A 0.5 ml aliquot of diluted inoculum containing an appropriate concentration of the test microorganism (1:100 dilution of the initial inoculum) was then added into each tube containing 0.5 ml serial dilutions of the test compound. After incubating for 2 days at 37° C., the tube was evaluated for visible growth. The MIC was determined as the lowest concentration of a compound which prevented visible microorganism growth. A culture growth control without compound (solvent only) and several culture sensitive reference agents were used as positive controls. The assays were performed in duplicate.

5.2.2. MINIMUM BIOCIDAL CONCENTRATION DETERMINATION

After determining the MIC, 0.1 ml of a ten-fold dilution from each tube showing no turbidity was plated onto chemical free nutrient agar plates. After 24 hours of incubation, the colonies were counted. The MBC was the lowest concentration of antibacterial compound that decreased the initial inoculum population by >99.9 percent. The initial population for E. coli. was $1\times10^7$–$6\times10^7$ colony forming units (CFU) per ml; for P. aeruginosa was $1\times10^6$–$5\times10^6$ CFU per ml; and for methicillin-resistant Staphylococcus aureus (MRSA) was $2\times10^6$–$7\times10^6$ CFU per ml.

5.2.3. SYNERGIC EFFECT STUDIES

Synergic effects of a putative potentiating substance in combination with an antibiotic reference compound were evaluated by a broth checkerboard method (Norden et al., J. Infect. Dis. 1979, 140, 629–633). Serial two-fold dilutions of the antibiotic reference compound in combination with a concentration of ½ MIC of the putative potentiating substance were made by the above described tube dilution method for determination of MICs and MBCs in each testing strain.

Since the potentiator is present at ½ of its MIC, the MIC determined for the antibiotic should be ½ of its usual value, if the effects of the two compounds are merely additive; greater than ½, if the compounds are antagonistic; and less than ½, if the compounds are synergistic. The "synergic effect" shown in the following Tables is the ratio of the MIC for the antibiotic alone to the MIC for the antibiotic in the presence of ½ MIC of the potentiator. A 2× synergic effect means that the activities of the antibiotic and potentiator are merely additive, whereas an effect greater than 2× indicates the occurrence of true synergy.

The invention is further described in the following examples which are in no way intended to limit the scope of the invention.

6. EXAMPLE 1

Synergic Effect of Gentamicin with anethole on Escherichia coli

Tests were performed to determine the synergic effect of anethole with Gentamicin on Escherichia coil (ATCC Results are given in Table 1. Gentamicin is known to be a mixture of 3 kinds of antibiotics which are extracted from Micromonospora purpurea. Gentamicin is one of most effective aminoglycoside antibiotics, but it has strong side effects, such as nephrotoxicity, ototoxicity, or neuromuscular blockade.

TABLE 1

| Testing Strain | Gentamicin Alone | Anethole Alone | Anethole (½ MIC) + Gentamicin | Synergic Effect |
|---|---|---|---|---|
| | MIC (µg/ml) | | | |
| Escherichia coli (ATCC 10536) | 0.78 | 400 | 0.049 | 16x |
| | MBC (µg/ml) | | | |
| Escherichia coli (ATCC 10536) | 0.78 | 800 | 0.049 | 16x |

7. EXAMPLE 2

Synergic Effect of Gentamicin with Indole or 2-Hexenal Potentiators

7.1. SYNERGIC EFFECTS OF GENTAMICIN WITH INDOLE OR 2-HEXENAL ON GRAM-NEGATIVE BACTERIA

Tests were performed to determine the synergic effect of indole or 2-hexenal with Gentamicin on gram-negative bacteria of the strains Escherichia coli (ATCC 10536) and Pseudomonas aeruginosa (ATCC 10145). Results are given in Table 2.

TABLE 2

| | MIC and MBC (µg/ml) | | | | | | | |
|---|---|---|---|---|---|---|---|---|
| Testing | Gentamicin Alone | | Indole Alone | | Indole (½ MIC) + Gentamicin | | Synergic Effect | |
| Strain | MIC | MBC | MIC | MBC | MIC | MBC | MIC | MBC |
| Escherichia coli (ATCC 10536) | 0.78 | 0.78 | 800 | 800 | 0.098 | 0.098 | 8x | 8x |
| Testing | Gentamicin Alone | | 2-Hexenal Alone | | Indole (½ MIC) + Gentamicin | | Synergic Effect | |
| Strain | MIC | MBC | MIC | MBC | MIC | MBC | MIC | MBC |
| Escherichia coli (ATCC 10536) | 0.78 | 0.78 | 200 | 200 | 0.20 | 0.20 | 4x | 4x |
| Testing | Gentamicin Alone | | Indole Alone | | Indole (½ MIC) + Gentamicin | | Synergic Effect | |
| Strain | MIC | MBC | MIC | MBC | MIC | MBC | MIC | MBC |
| Pseudomonas aeruginosa (ATCC 10145) | 0.39 | 0.78 | 400 | 800 | 0.049 | 0.20 | 8x | 4x |

TABLE 2-continued

| | MIC and MBC (µg/ml) | | | | | | | |
|---|---|---|---|---|---|---|---|---|
| Testing | Gentamicin Alone | | 2-Hexenal Alone | | Indole (½ MIC) + Gentamicin | | Synergic Effect | |
| Strain | MIC | MBC | MIC | MBC | MIC | MBC | MIC | MBC |
| Pseudomonas aeruginosa (ATCC 10145) | 0.39 | 0.78 | 200 | 200 | 0.20 | 0.39 | 2x | 2x |

7.2. SYNERGIC EFFECT OF GENTAMICIN WITH INDOLE OR 2-HEXENAL ON GRAM-POSITIVE BACTERIA

Tests were performed to determine the synergic effect of indole or 2-hexenal with Gentamicin on gram-positive bacteria on a methicillin-resistant strain of *Staphylococcus aureus* (ATCC 33591). Results are given in Table 3.

TABLE 3

| | MIC and MBC (µg/ml) | | | | | | | |
|---|---|---|---|---|---|---|---|---|
| Testing | Gentamicin Alone | | Indole Alone | | Indole (½ MIC) + Gentamicin | | Synergic Effect | |
| Strain | MIC | MBC | MIC | MBC | MIC | MBC | MIC | MBC |
| Methicillin-resistant Staphylococcus aureus (ATCC 33591) | 1.56 | 1.56 | 800 | 1600 | 0.39 | 0.39 | 4x | 4x |

TABLE 3-continued

| | MIC and MBC (µg/ml) | | | | | | | |
|---|---|---|---|---|---|---|---|---|
| Testing | Gentamicin Alone | | 2-Hexenal Alone | | 2-Hexenal (½ MIC) + Gentamicin | | Synergic Effect | |
| Strain | MIC | MBC | MIC | MBC | MIC | MBC | MIC | MBC |
| Methicillin-resistant Staphylococcus aureus (ATCC 33591) | 1.56 | 1.56 | 400 | 800 | 0.20 | 0.39 | 8x | 4x |

8. EXAMPLE 3

Synergic Effect of Tobramycin with Potentiators on MRSA

Tests were performed to determine the synergic effect of Tobramycin with Anethole, Indole or 2-Hexenal on Methicillin resistant *Staphylococcus aureus* (ATCC 33591). Results are given in Table 4. Tobramycin is derived from *Streptmyces tenebrarius*. In vitro tests demonstrate that the drug is bactericidal and that it acts by interfering with protein synthesis in bacterial cells. It exhibits a broad range of activity against gram-negative and gram-positive organisms. Tobramycin is also one of the most effective aminoglycoside antibiotics, but it has strong side effects, such as nephrotoxicity, ototoxicity, or neuromuscular blockade.

TABLE 4

| | MIC and MBC (µg/ml) | | | | | | | |
|---|---|---|---|---|---|---|---|---|
| Testing | Tobramycin Alone | | Anethole Alone | | Anethole (½ MIC:800) + Tobramycin | | Synergic Effect | |
| Strain | MIC | MBC | MIC | MBC | MIC | MBC | MIC | MBC |
| Methicillin-resistant Stapylococcus aureus: ATCC 33591 | 800 | 1600 | >1600 | >1600 | 100 | 800 | 8X | 2X |

| | Tobramycin Alone | | Indole Alone | | Indole (½ MIC) + Tobramycin | | Synergic Effect | |
|---|---|---|---|---|---|---|---|---|
| Testing | | | | | | | | |
| Strain | MIC | MBC | MIC | MBC | MIC | MBC | MIC | MBC |
| Methicillin-resistant Staphylococcus aureus: ATCC 33591 | 800 | 1600 | 800 | 1600 | 200 | 400 | 4X | 4X |

| | Tobramycin Alone | | 2-Hexenal Alone | | 2-Hexenal (½ MIC) + Tobramycin | | Synergic Effect | |
|---|---|---|---|---|---|---|---|---|
| Testing | | | | | | | | |
| Strain | MIC | MBC | MIC | MBC | MIC | MBC | MIC | MBC |
| Methicillin-resistant Staphylococcus aureus: ATCC 33591 | 800 | 1600 | 200 | 400 | 200 | 800 | 4x | 2x |

9. EXAMPLE 4

Synergic Effect of Amikacin with with [with] Potentiators on MRSA

Tests were performed to determine the synergic effect of Amikacin with Anethole, Indole or 2-Hexenal on Methicillin resistant *Staphylococcus aureus* (ATCC 33591). Results are given in Table 5. Amikacin is known to be a semisynthetic aminoglycoside antibiotic derived from kanamycin. In vitro studies indicate that the drug posesses a broad range of activity against gram-negative and gram-positive organisms. An important characteristic of Amikacin is that it resists degradation by most aminoglycoside-inactivating enzymes. Amikacin is also one of the most effective aminoglycoside antibiotics, but it has strong side effects, such as nephrotoxicity, ototoxicity, or neuromuscular blockade.

TABLE 5

MIC and MBC (µg/ml)

| Testing Strain | Amikacin Alone | | Anethole Alone | | Anethole (½ MIC:800) + Amikacin | | Synergic Effect | |
|---|---|---|---|---|---|---|---|---|
| | MIC | MBC | MIC | MBC | MIC | MBC | MIC | MBC |
| Methicillin-resistant *Staphylococcus aureus*: ATCC 33591 | 200 | 200 | >1600 | >1600 | 25 | 100 | 8x | 2x |

| Testing Strain | Amikacin Alone | | Indole Alone | | Indole (½ MIC) + Amikacin | | Synergic Effect | |
|---|---|---|---|---|---|---|---|---|
| | MIC | MBC | MIC | MBC | MIC | MBC | MIC | MBC |
| Methicillin-resistant *Staphylococcus aureus*: ATCC 33591 | 200 | 200 | 800 | 1600 | 25 | 50 | 8X | 4X |

| Testing Strain | Amikacin Alone | | 2-Hexenal Alone | | 2-Hexenal (½ MIC) + Amikacin | | Synergic Effect | |
|---|---|---|---|---|---|---|---|---|
| | MIC | MBC | MIC | MBC | MIC | MBC | MIC | MBC |
| Methicillin-resistant *Staphylococcus aureus*: ATCC 33591 | 200 | 200 | 200 | 400 | 25 | 50 | 8x | 4x |

The present invention is not to be limited in scope by the specific embodiments described herein. Indeed, various modifications of the invention in addition to those described herein will become apparent to those skilled in the art from the foregoing description and accompanying data. Such modifications are intended to fall within the scope of the claims. Various publications are recited herein, the disclosures of which are incorporated by reference herein in their entireties.

What is claimed:

1. A method for inhibiting the growth of MRSA, *E. coli* or *P. aeruginosa* comprising:
   contacting said microorganism with an aminoglycoside antibiotic selected from the group consisting of Gentamicin, Tobramycin and Amikacin, and a potentiator of antibacterial activity, wherein said potentiator is at least 200 µg/ml of anethole, at least 200 µg/ml of indole, or at least 100 µg/ml of 2-hexenal.

2. A pharmaceutical composition for the treatment of MRSA or *E. coli* infection comprising:
   an aminoglycoside antibiotic selected from the group consisting of Gentamicin, Tobramycin and Amikacin, and
   at least 200 µg/ml of an anethole potentiator of antibacterial activity.

3. A pharmaceutical composition for the treatment of MRSA, *E. coli* or *P. aeruginosa* infection comprising:
   an aminoglycoside antibiotic selected from the group consisting of Gentamicin, Tobramycin and Amikacin, and
   at least 200 µg/ml of an indole potentiator of antibacterial activity.

4. A pharmaceutical composition for the treatment of MRSA or *E. coli* infection comprising:
   an aminoglycoside antibiotic selected from the group consisting of Gentamicin, Tobramycin and Amikacin, and
   at least 100 µg/ml of a 2-hexenal potentiator of antibacterial activity.

5. A method for treatment of MRSA or *E. coli* infection comprising:
   contacting the infecting bacteria with an aminoglycoside selected from the group consisting of Gentamicin, Tobramycin and Amikacin, and at least 200 µg/ml of an anethole potentiator of antibacterial activity.

6. A method for treatment of MRSA, *E. coli* or *P. aeruginosa* infection comprising:
   contacting the infecting bacteria with an aminoglycoside selected from the group consisting of Gentamicin, Tobramycin and Amikacin, and at least 200 µg/ml of an indole potentiator of antibacterial activity.

7. A method for treatment of MRSA, or *E. coli* infection comprising:
   contacting the infecting bacteria with an aminoglycoside selected from the group consisting of Gentamicin, Tobramycin and Amikacin, and at least 100 µg/ml of a 2-hexenal potentiator of antibacterial activity.

* * * * *